United States Patent [19]

Owens et al.

[11] Patent Number: 5,642,726

[45] Date of Patent: Jul. 1, 1997

[54] REDUCED INTERNAL VOLUME NEONATAL SUCTION ADAPTOR

[75] Inventors: Warren D. Owens, Salt Lake City; Cary P. Jenkins, West Jordan, both of Utah; Ken Hargett, Galveston, Tex.

[73] Assignee: Alcove Medical, Inc., Salt Lake City, Utah

[21] Appl. No.: 631,675

[22] Filed: Apr. 9, 1996

Related U.S. Application Data

[63] Continuation-in-part of Ser. No. 324,687, Oct. 18, 1994, abandoned.

[51] Int. Cl.⁶ .................................................. A61M 16/00
[52] U.S. Cl. ..................... 128/200.26; 128/207.14; 128/207.15; 128/207.16; 128/912; 128/DIG. 26
[58] Field of Search .................. 128/200.26, 207.14, 128/207.15, 207.16, 912, DIG. 26

[56] References Cited

U.S. PATENT DOCUMENTS

| D. 312,880 | 12/1990 | Bodai et al. ................ D24/53 |
| 4,020,849 | 5/1977 | Jackson ...................... 128/351 |
| 4,193,406 | 3/1980 | Jinotti ...................... 128/204.18 |
| 4,240,417 | 12/1980 | Holever ..................... 128/203.12 |
| 4,351,328 | 9/1982 | Bodai ........................ 128/202.16 |
| 4,416,273 | 11/1983 | Grimes ...................... 128/207.16 |
| 4,510,933 | 4/1985 | Wendt et al. ............... 128/207.14 |
| 4,595,005 | 6/1986 | Jinotti ...................... 128/205.24 |
| 4,648,396 | 3/1987 | Raemer ...................... 128/204.22 |
| 4,836,199 | 6/1989 | Palmer ....................... 128/207.16 |
| 4,838,255 | 6/1989 | Lambert ...................... 128/202.16 |
| 4,850,350 | 7/1989 | Jackson ...................... 128/207.16 |
| 4,872,579 | 10/1989 | Palmer ...................... 128/205.19 |
| 4,909,248 | 3/1990 | McLennan Anderson ........ 128/207.14 |
| 4,967,743 | 11/1990 | Lambert ..................... 128/202.16 |
| 4,995,387 | 2/1991 | Jinotti ...................... 128/205.24 |
| 5,060,646 | 10/1991 | Page ......................... 128/207.14 |
| 5,062,420 | 11/1991 | Levine ....................... 128/204.18 |
| 5,088,486 | 2/1992 | Jinotti ...................... 128/207.14 |
| 5,140,983 | 8/1992 | Jinotti ...................... 128/207.14 |
| 5,184,611 | 2/1993 | Turnbull ..................... 128/207.14 |
| 5,255,672 | 10/1993 | Jinotti ...................... 128/200.26 |
| 5,269,756 | 12/1993 | Dryden ....................... 604/54 |
| 5,309,905 | 5/1994 | Teves ........................ 128/207.14 |
| 5,343,857 | 9/1994 | Schneider et al. ............ 128/202.27 |
| 5,349,950 | 9/1994 | Ulrich et al. ............... 128/207.16 |

OTHER PUBLICATIONS

"Operation and Clinical Application of the BEAR®NVM-1 Neonatal Volume Monitor", Kelvin D. MacDonald, RCP, Department of Respiratory Care, Kaiser Premanente Medical Center, Dec. 1991, pp. 1–19.

The BEAR CUB® Infant Ventilation System product brochure, InterMed.

Primary Examiner—Aaron J. Lewis
Attorney, Agent, or Firm—Madson & Metcalf

[57] ABSTRACT

A neonatal suction adaptor with reduced deadspace allows tidal volume monitoring and synchronization to continue without substantial interference while a suction catheter is used. The adaptor includes a central housing disposed about a central chamber. A ventilation connector and an endotracheal connector are each secured to, and extend from, the central housing. Each tubular connector defines a passage connected with the central chamber. The connectors are sized and shaped to form press-fit connections with endotracheal tubes and ventilation monitors. The endotracheal connector includes a sleeve separated from a core by an annular recess configured to receive part of an endotracheal tube ventilation adaptor. A suction access tube is also secured to, and extends from, the central housing. The suction access tube is connectable to a wide variety of standard sleeved or exposed suction catheters. The adaptor's deadspace is reduced by utilizing a narrow core passage, by receiving portions of conventional monitors and tubes into the ventilation connector passage and the endotracheal connector annular recess, and by filling potential deadspace with the core. A valve may be seated in the central chamber to further reduce the deadspace.

20 Claims, 8 Drawing Sheets

REDUCED INTERNAL VOLUME NEONATAL SUCTION ADAPTOR

RELATED APPLICATIONS

This application is a continuation-in-part of patent application Ser. No. 08/324,687 entitled REDUCED INTERNAL VOLUME NEONATAL SUCTION ADAPTOR filed Oct. 18, 1994, now abandoned.

FIELD OF THE INVENTION

The present invention relates to an adaptor for allowing suction catheter access to a neonatal ventilation circuit, and more particularly to a neonatal suction adaptor which has a reduced internal volume and which allows accurate and continuous tidal volume monitoring and ventilation synchronization during the introduction of a suction catheter into an endotracheal tube in a neonatal patient.

TECHNICAL BACKGROUND OF THE INVENTION

Figure 1:
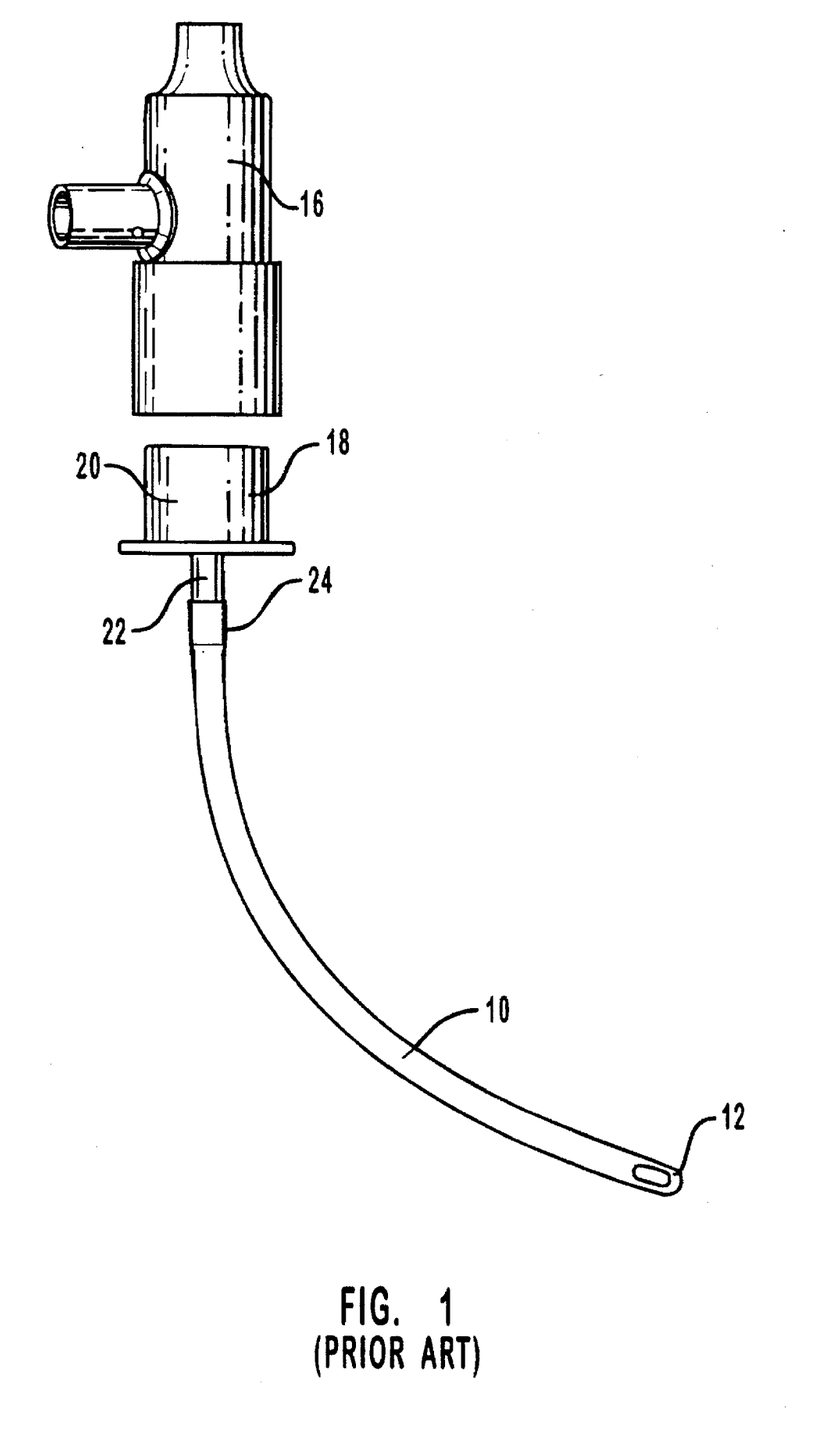
FIG. 1 is a perspective view illustrating a portion of a conventional ventilation circuit which includes an endotracheal tube, an endotracheal tube ventilation adaptor, and a ventilation monitor.

When an infant cannot breathe adequately without assistance, medical personnel may introduce a beveled end of an endotracheal tube into the infant's trachea. One conventional endotracheal tube 10 having a beveled end 12 is illustrated in FIG. 1. An external end 14 of the endotracheal tube 10 is connected to a mechanical ventilator (not shown) which pumps air through the endotracheal tube 10 into the infant's lungs, pauses while the infant exhales, and then repeats this cycle. The ventilator thus introduces oxygen-carrying air into the infant's lungs until such time as the infant is strong enough to breathe on its own. The amount of air pumped during each cycle is calculated according to the infant's lung capacity.

The ventilation system is preferably a "closed system." In a closed system, air pumped into the patient by the ventilator is cleaned to remove hazardous microorganisms. Also, a closed system has no substantial openings in the ventilation circuit through which microorganisms in the ambient environment can easily gain access to the interior of the endotracheal tube 10 and hence to the patient's lungs. In addition to reducing the risk of infection, a closed system is better suited for maintaining PEEP (positive end expiratory pressure) at the internal end 12 of the endotracheal tube 10 to ensure that the air pumped into the ventilation circuit by the ventilator actually reaches the patient's lungs.

To monitor PEEP and other important ventilation characteristics, modern ventilators include various monitoring devices such as the monitor 16 shown in FIG. 1. The monitor 16 is connectable to the endotracheal tube 10 by a conventional ventilation adaptor 18. The ventilation adaptor 18 includes a relatively large-diameter cylindrical extension 20 configured for press-fit connection to a ventilation circuit. The extension 20 is in fluid communication with a smaller-diameter tube 22 that is inserted in the external end 14 of the endotracheal tube 10.

The monitor 16 may be designed to monitor the "tidal volume," that is, the volume of air which moves as the infant inhales and exhales. Changes in tidal volume over time, or tidal volumes which lie outside the expected range, may indicate medical problems in the infant or mechanical problems with the ventilation circuit. The times at which air moves may also be monitored by the monitor 16 in order to synchronize the ventilator's pumping and pausing cycles with the infant's own breathing efforts. Synchronized ventilation has been shown to be more effective in oxygenating the patient's blood and less likely to cause significant damage to the patient's lungs.

In caring for infant patients, it is necessary to periodically suction out secretions which would otherwise accumulate in the infant's lungs. Suctioning is generally accomplished by introducing one end of a flexible suction catheter tube into the endotracheal tube and applying suction to the other end of the catheter tube. To reduce the extent of airway occlusion, the catheter tube is typically withdrawn from the endotracheal tube when the catheter is not in use.

The catheter tube may be an "exposed" catheter tube (not shown) whose only sterility-preserving enclosure is the manufacturer's packaging. An exposed catheter tube cannot be used without removing the tube from its packaging and thereby exposing the tube to an ambient environment which often contains potentially hazardous microorganisms.

Figure 2:
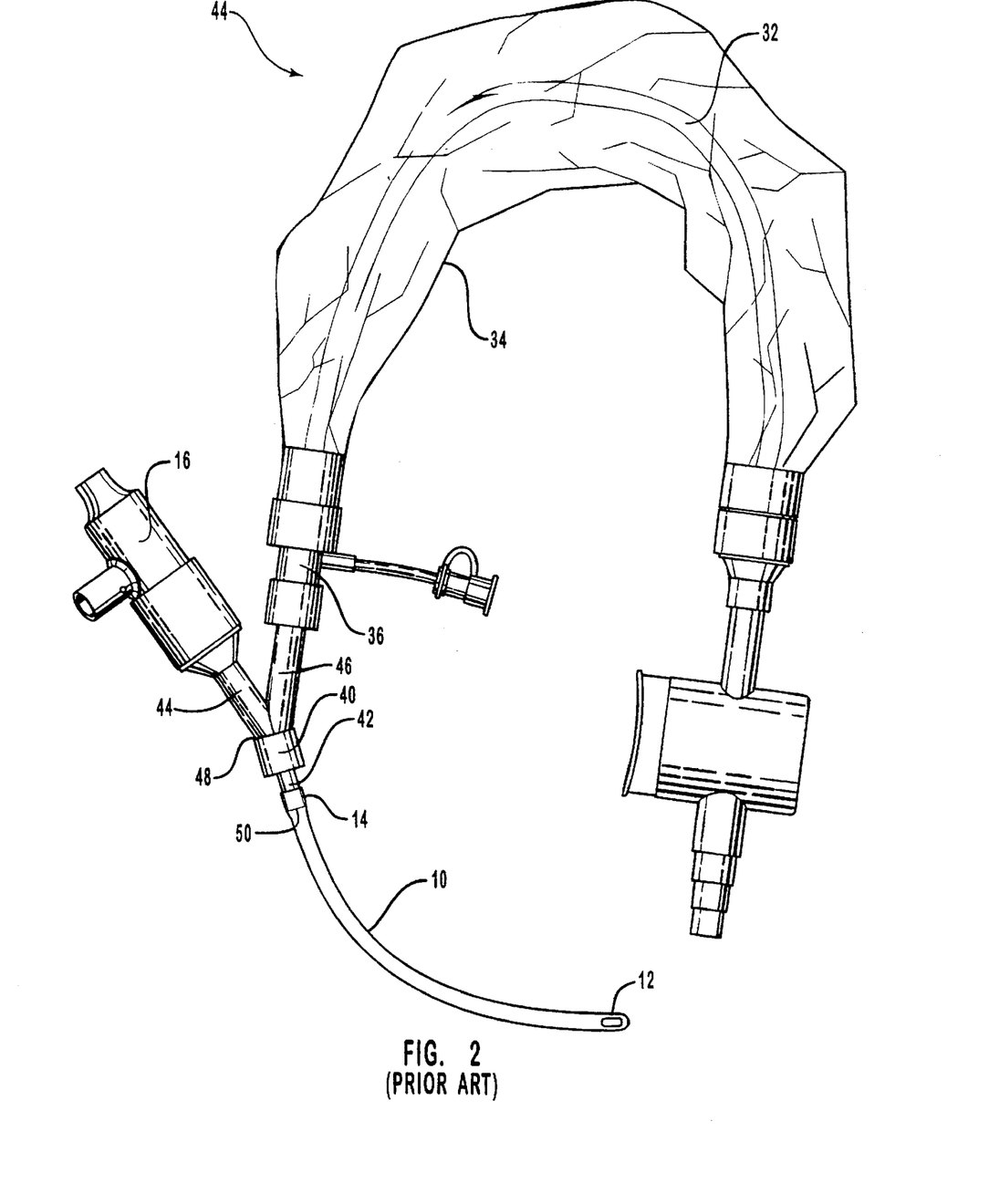
FIG. 2 is a perspective view illustrating a portion of a conventional ventilation circuit which includes an endotracheal tube, a Y-adaptor, a ventilation monitor, and a sleeved suction catheter.

In order to reduce the risk of introducing microorganisms into the infant's lungs during use of the suction catheter, many catheters are "sleeved." One conventional sleeved catheter is indicated generally at 30 in FIG. 2. In addition to a catheter tube 32, the sleeved catheter 30 includes a sterile sleeve or sack 34 which substantially encloses the catheter tube 32 to preserve the tube's sterility during use in a closed system. The sleeved catheter 30 also includes a fitting 36 for connecting the catheter 30 to a ventilation circuit.

Although a catheter tube (either sleeved or exposed) may be introduced by temporarily disconnecting a portion of the ventilation circuit to provide access to the endotracheal tube 10, this approach is not preferred. Opening the ventilation circuit interferes with proper ventilation of the infant. In some cases, opening a closed ventilator system leads to brain cell death from anoxia, or to cardiac irregularities such as bradycardia and cardiac arrest. Even if these severe consequences are avoided, opening the ventilation circuit breaches the system's sterility and thus creates a risk of infection in the infant. Introduction of the suction catheter should therefore interfere as little as possible with the continued ventilation of the infant, with the continuous monitoring of that ventilation, and with the sterility of the closed system.

To reduce the adverse impact of suction catheter usage on ventilation, various suction adaptors have been designed. One conventional adaptor, indicated at 40 in FIG. 2, includes three tubes 42, 44, and 46 which meet in a Y-shaped configuration. The bottom leg 42 of the Y-adaptor 40 includes an endotracheal connector which is insertable within the external end 14 of the endotracheal tube 10. One arm 44 of the Y includes a ventilation connector which is connectable to the ventilator by way of additional tubing. The other arm 46 of the Y includes a suction access tube which provides the neonatal suction catheter 30 with access to the endotracheal tube 10. Like the monitor 16 and other devices designed for connection to a ventilation circuit, the Y-adaptor 40 is typically attached to the circuit by press-fit connections which are held in place by friction.

In theory, the Y-adaptor 40 would allow the suction catheter tube 32 access to the endotracheal tube 10 without interrupting ventilation and monitoring, and without opening a sterile closed system. Medical personnel would feed the catheter tube 32 down through the suction access tube 46, into the endotracheal connector 42, and from there into the endotracheal tube 10. The catheter 30 would remain attached to the Y-adaptor 40 and the tube 32 would be withdrawn into its sterile sleeve 34 when not in use, so there would be no need to disconnect the ventilator and the system would remain closed during suction catheter usage.

In practice, however, the endotracheal tube 10 is often inserted in the infant with the ventilation adaptor 18 securely attached to the external end 14 of the endotracheal tube as shown in FIG. 1. Thus, in order to suction the infant's airway it is necessary to remove the endotracheal adaptor 18 from the endotracheal tube 10 and replace it with the Y-adaptor 40 as shown in FIG. 2.

Removing the ventilation adaptor 18 and attaching the Y-adaptor 40 to the endotracheal tube 10 poses numerous risks for the infant. The removal necessarily interrupts ventilation, and thus increases the risk of brain anoxia or cardiac irregularities. The removal also breaches the sterility of the system, thereby increasing the risk of infection. In addition, the twisting, pulling and pushing actions required to replace the ventilation adaptor 18 with the Y-adaptor 40 may cause the endotracheal tube 10 to bruise the infant's breathing passages.

Even if these problems are avoided, maneuvering the catheter tube 32 around the bend 48 between the arm 46 and the leg 42 of the Y-adaptor 40 may cause a kink in the endotracheal tube 10 at or near the edge 50 of the Y-adaptor 40 that interferes with ventilation. Such maneuvering may also cause a kink in the catheter tube 32 that interferes with suctioning.

Accordingly, some conventional suction adaptors are "straight" adaptors which allow the catheter tube to travel in a substantially straight line in or out of the endotracheal tube. A straight adaptor includes a suction access tube that provides endotracheal tube access to a suction catheter. The straight adaptor also includes a tubular endotracheal connector that is connectable to the ventilation adaptor of an endotracheal tube, and a tubular ventilation connector that is connectable to a ventilator. The suction access tube and the endotracheal connector are substantially aligned in that their central longitudinal axes are collinear.

Thus, the straight adaptor is essentially a Y-adaptor in which the leg and one arm of the Y have been moved into alignment, and which connects to the endotracheal tube ventilation adaptor rather than connecting directly to the endotracheal tube. The straight adaptor avoids the problems created by the bend between a Y-adaptor's arm and leg by simply removing the bend. The straight adaptor avoids the problems created by removal of the endotracheal tube ventilation adaptor by connecting to that adaptor rather than removing and replacing it.

However, straight adaptors, Y-adaptors, and other conventional suction adaptors all derive their internal configurations from suction adaptors that are intended for use in treating adult patients rather than neonates. As a consequence, conventional neonatal suction adaptors have a relatively large effective internal volume, which in turn increases the effective internal volume of the entire ventilation circuit. The effective internal volume of an adaptor or a ventilation circuit is also known as the "deadspace" of the adaptor or the circuit, respectively.

The deadspace includes spaces inside the ventilation circuit which are in fluid communication with the infant's lungs. If the amount of deadspace is too great, the infant's exhalations will not be substantially cleared from the ventilation circuit but will rather remain behind in the deadspace. This previously breathed air will then be re-inhaled on the infant's next breath. If the infant rebreathes too great a portion of its exhalations, the infant will retain carbon dioxide rather than receiving oxygen. Brain anoxia, cardiac irregularities, and death may follow.

Likewise, if the ventilation circuit contains excessive deadspace, the ventilator will ventilate the deadspace rather than ventilating the infant's lungs. Oxygenated air will be pumped into the ventilation circuit by the ventilator during "inhalation," but rather than being inhaled by the infant, the oxygenated air will remain within the deadspace. On exhalation, the oxygenated air will be expelled from the circuit without ever having reached the infant.

Adequate ventilation of an infant is generally difficult or impossible if the amount of deadspace inside the ventilation circuit exceeds about one-third of the infant's tidal volume. The tidal volume of a neonatal patient is typically in the range from about three to about six cubic centimeters per pound of body weight. For instance, an infant weighing about 1000 grams (about two pounds) normally has a tidal volume in the range from about six to about 12 cubic centimeters.

Because neonatal patients have significantly smaller tidal volumes than other patients, they are significantly more sensitive than other patients to small changes in the volume of deadspace within an adaptor. A change of one or two cubic centimeters in the deadspace of an infant's ventilation circuit may mean the difference between life and death. For instance, a ventilation circuit having five cubic centimeters of deadspace could be fatal to a two-pound infant which is effectively ventilated once the circuit's deadspace is reduced to three cubic centimeters.

The need to reduce deadspace is not even recognized in conventional neonatal suction adaptors, much less adequately addressed. The ventilator connectors, endotracheal tube connectors, and suction access tubes of conventional neonatal adaptors are configured merely with a view toward providing press-fit connections to standard size ventilator tubes, endotracheal tubes, sleeved catheters, and other devices. Thus, the internal dimensions of these elements of conventional adaptors often contribute excessive deadspace to the ventilation circuit. Likewise, many conventional straight adaptors include additional tubes or connectors which allow temperature sensors, pressure sensors, and other devices to be connected to the adaptor. These additional tubes increase the deadspace of the ventilation circuit by providing volumes which may trap oxygenated air intended for the infant or volumes which may trap the infant's exhalations and permit excessive rebreathing of those exhalations.

Thus, it would be an advancement in the art to provide a neonatal suction adaptor which has less deadspace than conventional adaptors.

It would also be an advancement in the art to provide such a neonatal suction adaptor which allows a catheter tube to travel substantially unobstructed in and out of the endotracheal tube.

It would be a further advancement to provide such a neonatal suction adaptor which is easily connected with a wide variety of conventional sleeved catheters, ventilation monitors, and endotracheal tubes to form a closed system.

It would be an additional advantage to provide such a neonatal suction adaptor which allows the use of a suction catheter without substantial interruption of neonatal tidal volume monitoring and synchronization.

Such a neonatal suction adaptor is disclosed and claimed herein.

BRIEF SUMMARY OF THE INVENTION

The present invention provides a neonatal suction adaptor which permits tidal volume monitoring and synchronization in a ventilation circuit. The adaptor has a smaller effective internal volume than conventional adaptors, and thus is particularly well-suited for use in treating patients with relatively small lung capacity. As explained below, the adaptor's effective internal volume is reduced by employing various means, including utilizing narrow catheter tube passages, by employing a flexible valve, and by filling potential deadspace with portions of the adaptor or with portions of conventional devices to which the adaptor is connected. The use of such means for substantially reducing and minimizing deadspace is of significance in providing an adaptor which is particularly usable in treating neonatal infants.

As used herein, the terms "substantially reduce" or "substantially minimize" deadspace will refer to configuring the device such that little excess deadspace remains in the device once it is attached to the components necessary to place it in operation. For example, deadspace is substantially minimized or substantially reduced within a central housing if the device is configured such that a suction catheter can freely pass through the central housing, but such that there is very little additional volume. In that regard, if deadspace within the central housing is maintained below about 1 cubic centimeter, the deadspace has been substantially reduced and substantially minimized. In particular, deadspace of between about 0.4 cc and 1.0 cc is presently preferred when using the embodiments of the invention illustrated and described herein. In particular, deadspace between about 0.4 cc and 0.6 cc is found to be acceptable. Deadspace is also substantially minimized and substantially reduced by employing the means mentioned in the preceding paragraph. Those means will be more fully discussed below.

One embodiment of the suction adaptor includes a central housing which substantially defines a central chamber. The exterior of the central housing may have two opposing grooves for releasably engaging the arms of a U-shaped adaptor holder. The adaptor holder secures the adaptor during suction catheter manipulation to reduce the risk of accidentally opening the closed ventilation circuit or bruising the patient's breathing passages. The central housing and the remainder of the adapter are preferably molded in one piece from plastic or a similar conventional material.

An endotracheal connector and a ventilation connector are each secured to, and extend from, the central housing. Each connector is generally tubular in shape, and each defines a passage which is preferably in continuous fluid communication with the central chamber. The endotracheal and ventilation connectors are sized and shaped to releasably engage a conventional endotracheal tube and a conventional ventilation monitor, respectively. The connectors are preferably configured to releasably engage these standard devices by using friction to form press-fit connections. These connectors also include means for securing other components of the respiratory circuit, while at the same time substantially minimizing the deadspace produced by said connection.

The endotracheal connector includes a sleeve which is disposed about a core. The sleeve and the core are separated by an annular recess. The endotracheal connector is preferably configured to form a press-fit connection with a conventional endotracheal tube by receiving within the annular recess a cylindrical extension of a conventional endotracheal tube ventilation adaptor. Placement of a portion of the extension within the annular recess reduces the contribution of the annular recess to the effective internal volume of the adaptor.

The core has a core passage which is in fluid communication with the central chamber and which is capable of providing a catheter tube with access to an attached endotracheal tube. In order to reduce the effective internal volume of the adaptor, the core passage is smaller than passages traversed by catheter tubes in conventional adaptors. The core passage preferably has a diameter of about four millimeters. Thus, the core passage is preferably only large enough to allow passage of an 8 French or smaller neonatal catheter tube without occluding the passage. The total volume of the central chamber and the core passage is preferably no greater than about one cubic centimeter, and is most preferably in the range from about 0.4 to about 0.6 cubic centimeters.

The ventilation connector includes a tube which has a ventilation passage that is in fluid communication with the central chamber. To reduce deadspace, the ventilation connector tube is capable of receiving within itself at least a portion of an inner tube of a conventional ventilation monitor. An outer tube of the ventilation monitor receives a portion of the ventilation connector to form a press-fit connection.

A suction access tube is also secured to, and extends from, the central housing. The suction access tube defines an additional passage which is preferably placed in fluid communication with the central chamber only during suction catheter usage. The suction access tube has a suction access passage that is in fluid communication with said central chamber. The device is configured such that a catheter tube may travel along a substantially unobstructed path down the suction access passage in or out of the core passage and hence in or out of an endotracheal tube connected to the adaptor.

The suction access tube preferably can optionally provide universal access for neonatal suction catheters. Thus, the suction access tube is preferably sized and shaped to form the male portion of a press-fit connection with all standard sleeved neonatal suction catheters. The suction access tube is preferably also configured to receive standard exposed neonatal suction catheters. In addition, the access tube is configured in such a manner as to reduce deadspace and maintain a closed system when no catheter is in use.

At least a portion of the suction access passage may be separated from at least a portion of the central chamber by a valve. In one embodiment, the valve is a flexible "duckbill" valve which is seated in a valve recess in the central housing. The valve is positioned to restrict air flow from the central chamber into the suction access passage without preventing suction catheter access. When the catheter is not in use, the catheter tube is retracted out of the central chamber and the valve is fully closed.

To allow suction catheter usage, the catheter tube is easily passed through the mouth of the valve into the central chamber and from there into the core passage and the endotracheal tube. The valve is flexible and resilient, so it tends to close about the catheter tube during suction catheter usage rather than opening fully. This tendency reduces deadspace in the circuit and allows maintenance of PEEP at the internal end of endotracheal tube as the suction catheter is used.

Thus, the neonatal suction adaptor of the present invention has several advantageous features. The adaptor has a smaller effective internal volume than conventional neonatal suction adaptors, thereby making the adaptor suitable for use with smaller patients than those for which conventional adaptors are appropriate. The reduction in deadspace is accomplished by various means such as utilizing a narrow core passage, employing a flexible valve to separate the suction access passage from the central chamber, receiving portions of conventional monitors and tubes into the ventilation connector passage and the endotracheal connector annular recess, and filling potential deadspace with the core. Thus, various components of the respiratory support system can be attached to the device while minimizing the deadspace produced by such a connection.

In addition, the suction access passage and the core passage are aligned to permit a catheter tube to travel in a substantially unobstructed manner in and out of the endotracheal tube, thereby reducing the risk of kinks in the catheter tube and the endotracheal tube. The adaptor is also easily connected by press-fit connections with a wide variety of sleeved neonatal suction catheters, ventilation monitors, and endotracheal tubes to form a closed system. Moreover, the adaptor allows tidal volume monitoring and synchronization to continue without substantial interference while a suction catheter is used, thereby reducing the risk of anoxia, heart failure, pressure necrosis, and other adverse effects of conventional adaptor usage.

These and other features and advantages of the present invention will become more fully apparent through the following description and appended claims taken in conjunction with the accompanying drawings.

BRIEF DESCRIPTION OF THE DRAWINGS

In order that the manner in which the above-recited and other advantages and features of the invention are obtained, a more particular description of the invention summarized above will be rendered by reference to the appended drawings. Understanding that these drawings only provide a selected embodiment of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Reference is now made to the figures wherein like parts are referred to by like numerals. The present invention relates to a neonatal suction adaptor which permits tidal volume monitoring and synchronization in a ventilation circuit. One embodiment of a neonatal suction adaptor according to the present invention is designated generally at 100 in FIGS. 3 through 5. The adaptor 100 includes a central housing 102 which substantially defines a central chamber 104 (shown best in FIGS. 4 and 5). Deadspace within the housing is substantially minimized and reduced by configuring wall 105 in such a manner that it extends into the chamber 104 and occupies space which would other wise constitute excess deadspace.

The exterior of the central housing 102 preferably has two opposing grooves 106, 108 for releasably engaging the arms of a U-shaped adaptor holder (not shown). The adapter 100 is preferably molded in one piece from plastic, k-resin, or a similar conventional material.

An endotracheal connector 120 is secured to and extends from the central housing 102. The endotracheal connector 120 is preferably an integral extension unitary with the central housing 102. The endotracheal connector 120 is generally tubular in shape and defines a passage 122 which is preferably in continuous fluid communication with the central chamber 104. The passage 122 preferably defines a central longitudinal axis 124. The endotracheal connector 120 is sized and shaped to releasably engage a conventional endotracheal tube ventilation adaptor 18. The endotracheal connector 120 is preferably configured to releasably engage the ventilation adaptor 18 by using friction to form a press-fit connection.

The endotracheal connector 120 includes a sleeve 126 which is disposed about a core 128. The sleeve 126 and the core 128 are separated by an annular recess 130. The endotracheal connector 120 is configured to form a press-fit connection with the endotracheal tube ventilation adaptor 18 by receiving within the annular recess 130 the cylindrical extension 20 of the ventilation adaptor 18 as shown in FIG. 3.

Because the core 128 fits within the cylindrical extension 20 of the ventilation adaptor 18, connecting the adaptor 100 to a ventilation circuit actually reduces the deadspace in the circuit. Thus configured, the core 128 occupies about 0.22 cubic centimeters of volume that would otherwise be deadspace. In this manner, the device 100 is provided with means for substantially minimizing the deadspace in the connection between the endotracheal tube 10 and the endotracheal connector 120.

Figure 3:
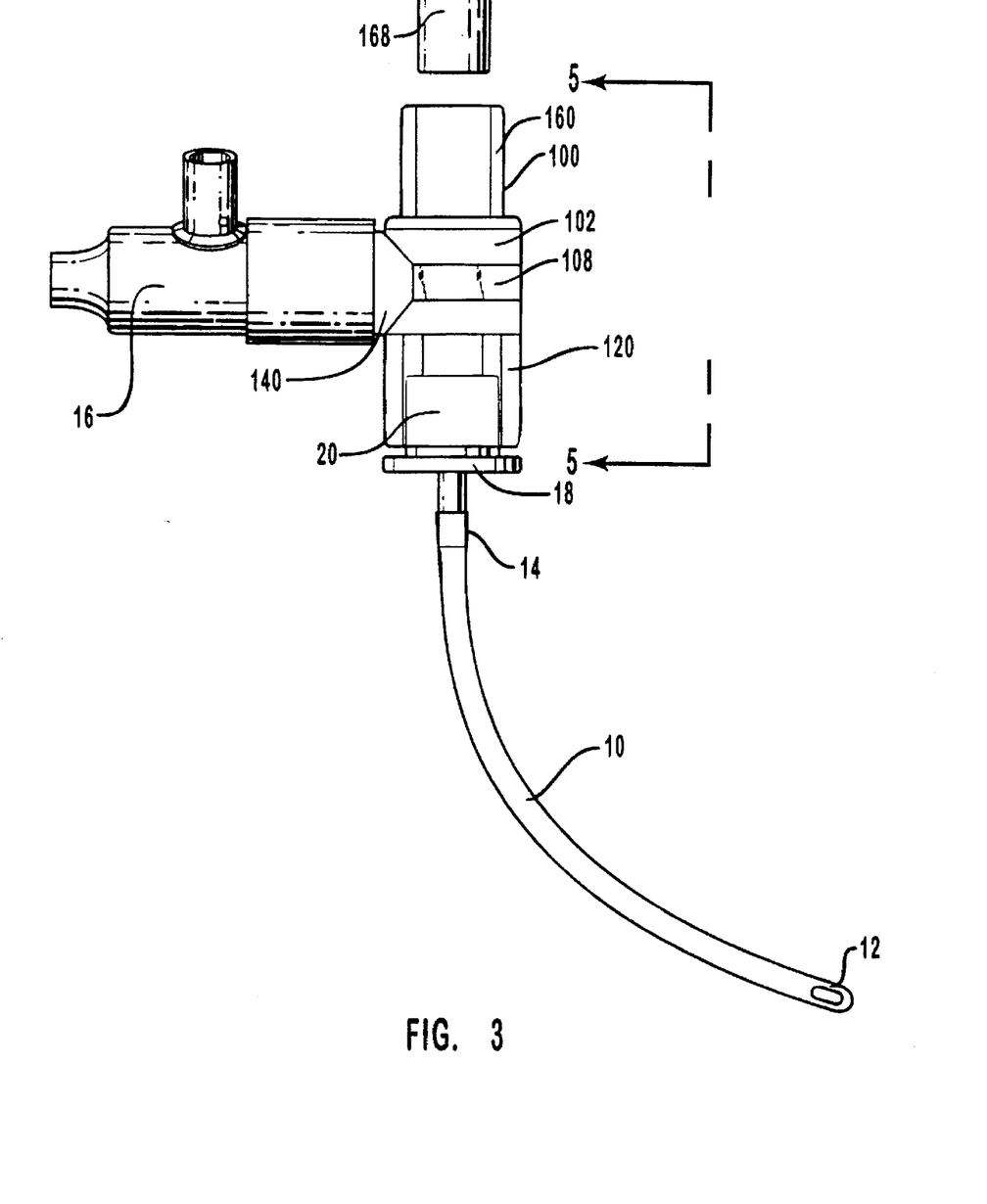
FIG. 3 is a side perspective view illustrating a portion of a ventilation circuit which includes an endotracheal tube, an endotracheal tube ventilation adaptor, a neonatal suction adaptor according to the present invention, a ventilation monitor, and a neonatal suction adaptor plug according to the present invention.
Figure 4:
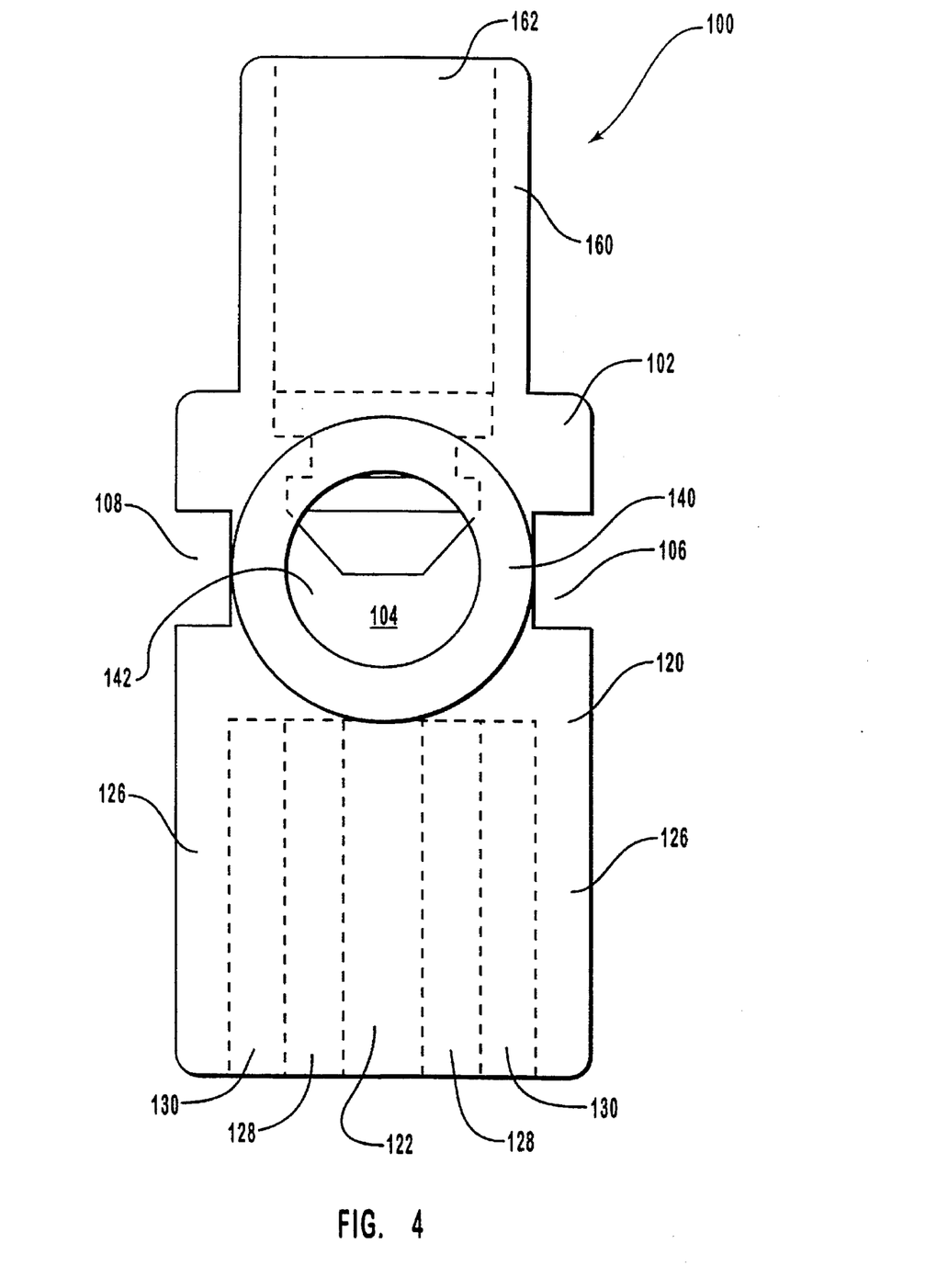
FIG. 4 is an end view further illustrating the neonatal suction adaptor shown in FIG. 3.
Figure 5:
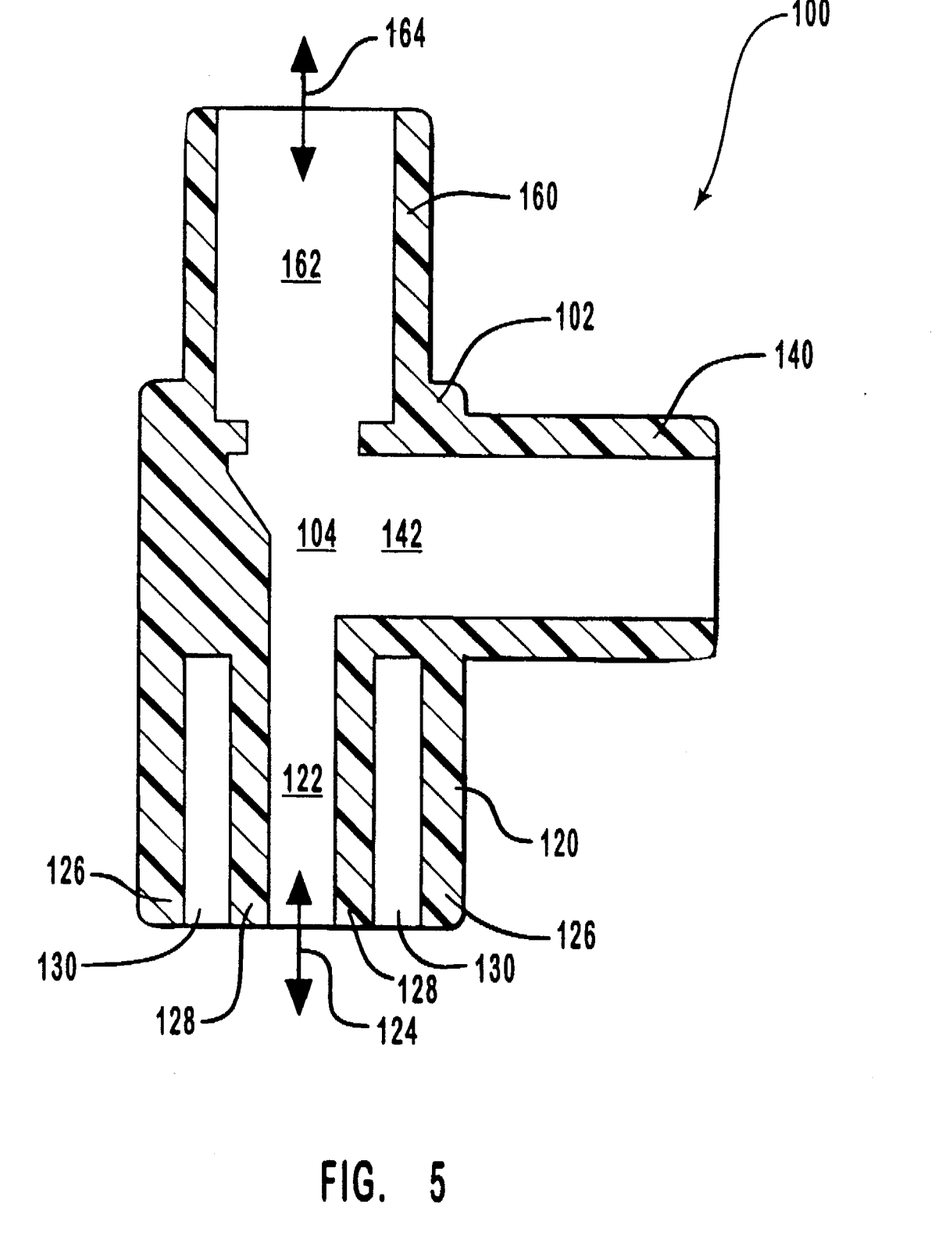
FIG. 5 is a side cross-sectional view taken along line 5—5 in FIG. 3, further illustrating the neonatal suction adaptor.

With continued reference to FIGS. 3 through 5, the core 128 substantially surrounds the core passage 122 which is in fluid communication with the central chamber 104. The passage 122 is capable of providing a catheter tube 32 (FIG. 2) with access to an attached endotracheal tube 10. In order to reduce the effective internal volume of the adaptor 100, the core passage 122 is smaller than passages traversed by catheter tubes in conventional adaptors. The core passage 122 preferably has a diameter of about four millimeters. Thus, the core passage 122 is preferably only large enough to allow passage of an 8 French or smaller neonatal catheter tube without occluding the passage 122. The total volume of the central chamber 104 and the core passage 122 is preferably no greater than about one cubic centimeter, and is most preferably in the range from about 0.4 to about 0.6 cubic centimeters.

Figures 6, 7:
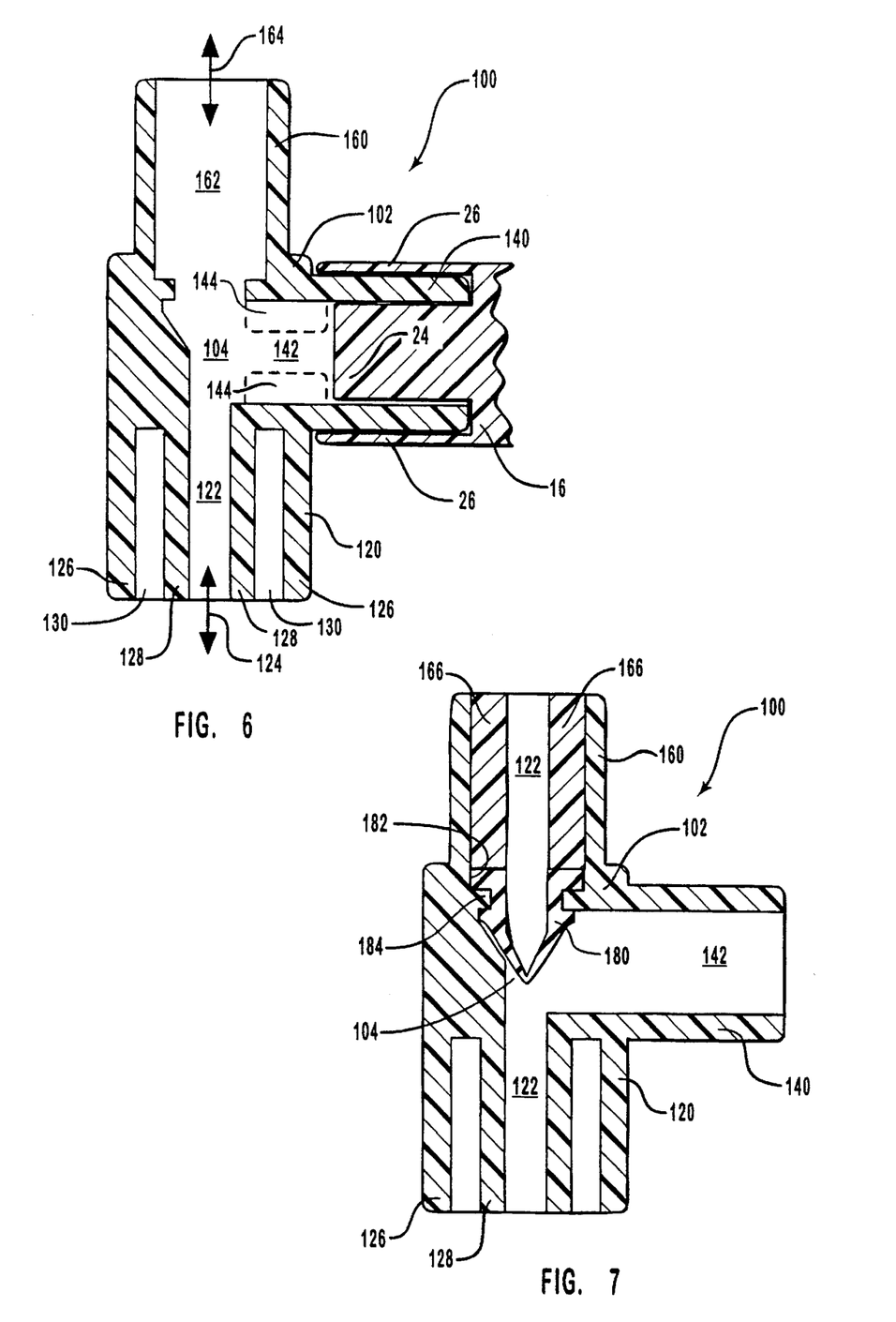
FIG. 6 is a side cross-sectional view as in FIG. 5, illustrating a conventional ventilation monitor connected to the neonatal suction adaptor.
FIG. 7 is a side cross-sectional view as in FIG. 5, illustrating a valve and a reducer tube placed within the neonatal suction adaptor.

A ventilation connector 140 is also secured to and extends from the central housing 102. The ventilation connector 140 is preferably an integral extension unitary with the central housing 102. The ventilation connector 140 is generally tubular in shape and defines a passage 142 which is preferably in continuous fluid communication with the central chamber 104. In some embodiments, a portion of the passage 142 is narrowed near the central chamber 104 by an inwardly extending ring 144 as shown in phantom in FIG. 6. The ventilation connector 140 is sized and shaped to releasably engage a conventional ventilation monitor 16 as shown in FIGS. 3 and 6. The ventilation connector 140 is preferably configured to releasably engage the monitor 16 or conventional ventilation circuit tubing (not shown) by using friction to form a press-fit connection.

As illustrated in FIGS. 3-7, the adaptor 100 is T-shaped, with the ventilation passage 142 being perpendicular to the core passage 122. The ventilation connector tube 140 is capable of receiving within itself at least a portion of an inner tube 24 of a conventional ventilation monitor 16 as illustrated in FIG. 6. An outer tube 26 of the ventilation monitor 16 receives a portion of the ventilation connector 140 to form a press-fit connection. A portion of the passage 142 is further occupied in some embodiments by the ring 144, which is shown in phantom in FIG. 6. The diameter of the open passage 142 within the ring 144 is preferably about seven millimeters. Thus, the adaptor 100 has even less deadspace than is shown in FIG. 5, because a portion of the passage 142 is occupied by the inner tube 24 and/or the ring 144. In this manner the device is provided with means for substantially minimizing the deadspace in the connection between the endotracheal connector and the ventilator (or monitor 16).

As shown in FIGS. 3 through 5, a suction access tube 160 is also secured to, and extends from, the central housing 102. The suction access tube 160 defines an additional passage 162 which may be placed in fluid communication with the central chamber 104 only during suction catheter usage. Suction catheter "usage" occurs during periods in which the suction catheter tube 32 (FIG. 2) is being positioned in the adaptor 100 or the endotracheal tube 10, as well as during periods in which suction is being applied to the suction catheter tube 32 to remove undesired material from the patient's airway.

The suction access tube 160 extends from the central housing 102 in a direction generally opposite to the endotracheal connector 120. The suction access tube 160 preferably defines a central longitudinal axis 164 of the suction access passage 162. The axis 164 is preferably substantially parallel to, and preferably collinear with, the central longitudinal axis 124 of the core passage 122. Thus, the catheter tube 32 (FIG. 2) may travel along a substantially straight path down the suction access passage 162 in or out of the core passage 122 and hence in or out of the endotracheal tube 10 connected to the adaptor 100.

The suction access tube 160 preferably provides universal access for neonatal suction catheters, including both sleeved catheters such as the catheter 30 (FIG. 2) and exposed catheters (not shown). Thus, the suction access tube 160 is preferably sized and shaped to form the male portion of a press-fit connection with all standard sleeved neonatal suction catheters. In addition, the suction access tube 160 is preferably configured to form the female portion of a connection with a conventional sleeved suction catheter or a conventional exposed suction catheter.

As shown in FIG. 7, the access tube 160 may receive a thick-walled reducer tube 166 to reduce deadspace when exposed catheters are used. In the embodiment shown, the reducer tube 166 is removable, but in an alternative embodiment the reducer tube 166 is permanently secured to the access tube 160. As shown in FIG. 3, the access tube 160 is also preferably configured to receive a plug 168. The plug 168 reduces deadspace within the passage 162 (FIG. 4), and also assists in maintaining a closed system when no suction catheter is in use. The reducer tube 166 and the plug 168 are preferably formed of the same or similar materials as the material used in the central housing 102, the tube 160, and the connectors 140 and 120.

As illustrated in FIG. 7, at least a portion of the suction access passage 162 is preferably separated from at least a portion of the central chamber 104 by a valve 180. Although the valve 180 is shown in an adaptor configured with a reducer tube 166, the valve 180 may also be used when no reducer tube is present. The valve 180 is preferably a flexible "duckbill" valve. The valve 180 is preferably seated in a valve recess 182 in the central housing 102, and is preferably held in place by a flange 184.

With reference to FIGS. 2, 3, and 7, the valve 180 is thus positioned to restrict air flow between the central chamber 104 and the suction access passage 162 without preventing suction catheter access to the core passage 122. When the catheter tube 32 is not in use, the catheter tube 32 is retracted out of the central chamber 104 and the valve 180 is fully closed. The valve 180 is preferably shaped, positioned, and formed of flexible material, such that the catheter tube 32 is easily passed through the mouth of the valve 180 in or out the central chamber 104 and from there into the core passage 122 and the endotracheal tube 10. The valve 180 is preferably resilient so that it tends to close about the catheter tube 32 during suction catheter usage. Such closure reduces deadspace in the ventilation circuit and allows maintenance of PEEP at the internal end 12 of endotracheal tube 10 as the suction catheter is used.

Thus configured, the valve 180 reduces the effective internal volume of the adaptor 100 in several ways. The valve 180 itself occupies volume within the central chamber 104. In some embodiments, the valve 100 also occupies volume within the suction access passage 162. In addition, when the suction catheter is not in use, and to some extent even when the suction catheter is in use, the valve 180 separates the suction access passage 162 from the central chamber 104 and other portions of the ventilation path and thus reduces the contribution of the access passage 162 to the effective internal volume of the adaptor 100.

With reference to FIGS. 3, 6, and 7, the adaptor 100 is most preferably configured with the cylindrical extension 20 of the ventilation adaptor 18 substantially fully inserted in the recess 130 such that the core 128 occupies space within the extension 20 that would otherwise be deadspace in the ventilation circuit. In addition, the adaptor 100 is most preferably configured with a valve such as the valve 180 and with thickened walls such as the solid ring 144 in order to further decrease deadspace. However, those of skill in the art will appreciate that various combinations of the features of the present invention may be employed to provide a reduced internal volume neonatal suction adaptor that is most suitable in a given situation. In any event, each of the connections to the device is made in such a manner as to substantially minimize the deadspace within the device.

Finally, the central chamber 104 is also configured to minimize deadspace. The chamber is configured such that it is only large enough to perform the required functions. For example, the chamber is only sufficiently large to allow unobstructed passage of a suction catheter through the chamber 104. As illustrated in FIGS. 5–7, internal chamber 104 is provided with a tapered wall 105 which acts as a seat for the valve 180, and also minimizes the deadspace within the device. Thus, the device 100 substantially eliminates unnecessary space within the chamber 104, unlike conventional adaptors.

Figure 8:
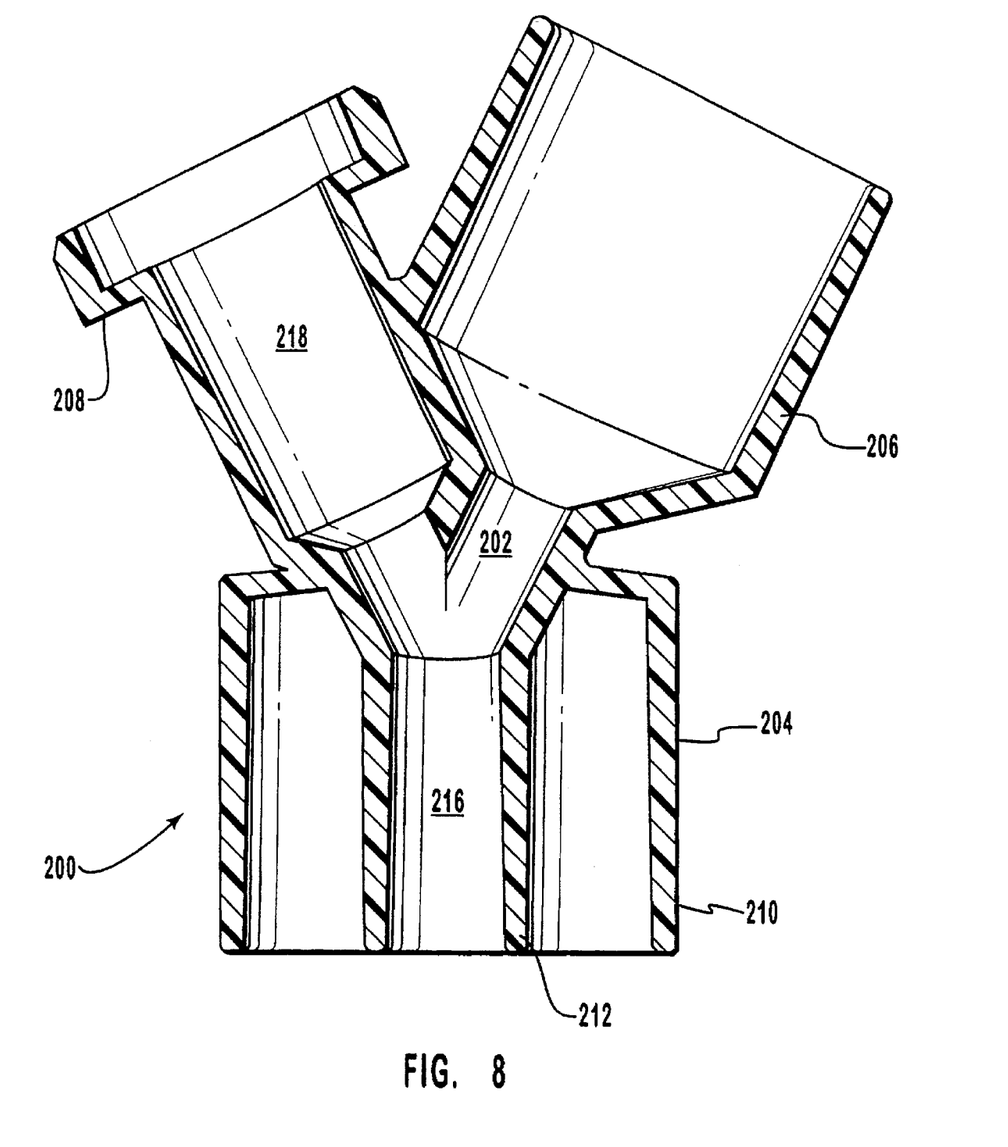
FIG. 8 is a cross-sectional view of a further embodiment of the present invention.
Figure 9:
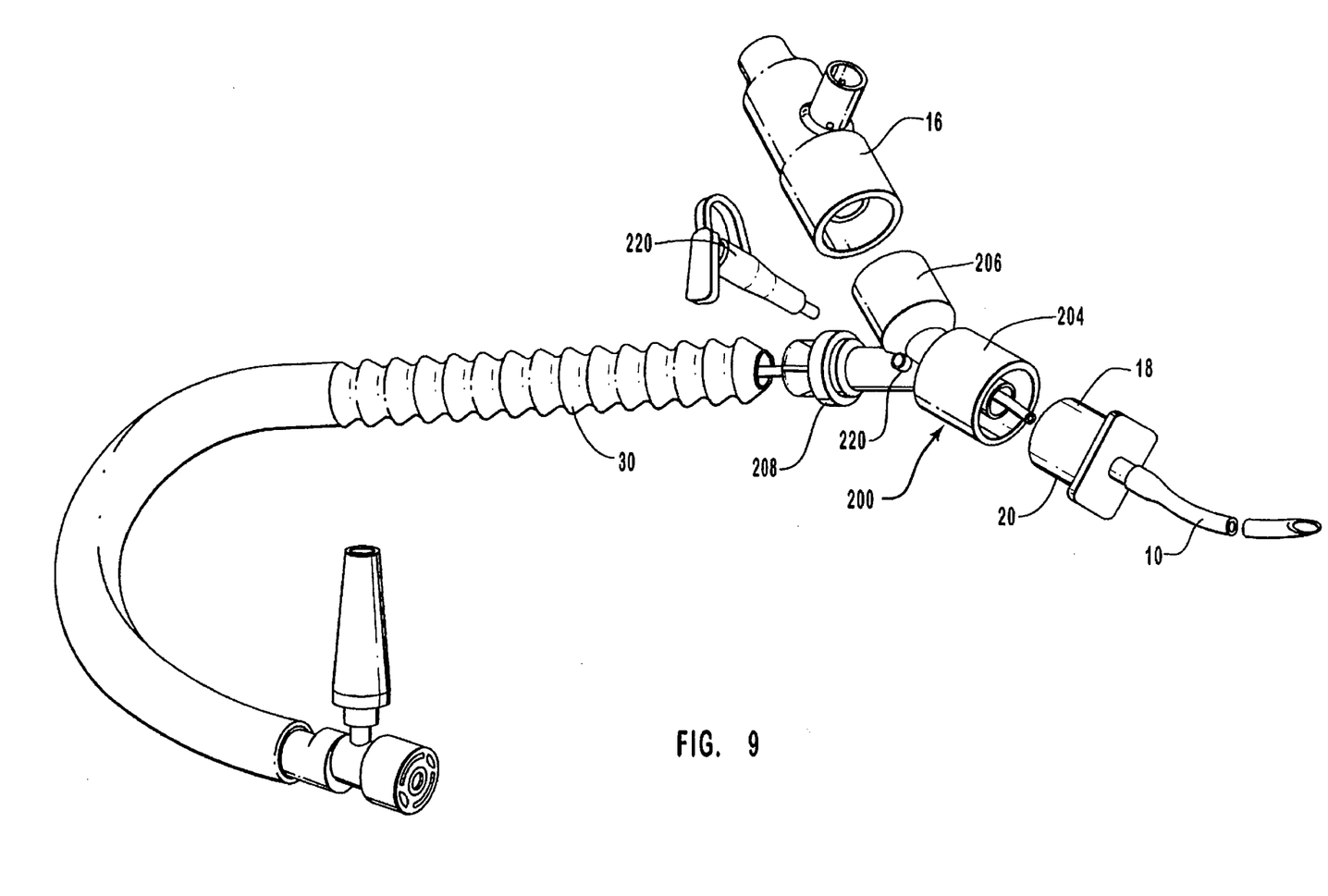
FIG. 9 is an exploded perspective view of a ventilation circuit employing the embodiment of the device illustrated in FIG. 8.

A further preferred embodiment of the device 200 is illustrated in FIGS. 8 and 9. In this embodiment, the device takes on a generally Y-shaped configuration. At the same time each of the inventive features discussed above it incorporated into this embodiment of the device 200. The device 200 is generally comprised of a central housing 202, an endotracheal connector 204, a ventilator connector 206, and a suction access tube 208.

As with the previously described embodiment of the device, the endotracheal connector 204 of device 200 comprises an outer sleeve 210. Positioned within the interior of sleeve 210 is a core 212. Sleeve 210 and core 212 together define a recess 214. As with the embodiment of the device described with reference to FIGS. 3–7, the sleeve 210 and core 212 are configured such that a conventional ventilation adaptor 18 can be press fit into the recess 214. Thus, the endotracheal connector 204 is provided with means for minimizing the deadspace when the adaptor 18 is removably connected. In essence, the adaptor 18 and the core 212 occupy substantially all of the unnecessary deadspace within this connection. The passage 216 defined by the core is specifically configured such that a suction catheter can freely move through the passage 216, but such that wasted space within the passage 216 is substantially eliminated.

The device 200 is also provided with a ventilation connector 206. Ventilation connector 206 is similar in design and configuration to ventilation connector 140 described above. Ventilation connector 206 is design to receive a conventional monitor 16 or to attach directly to a ventilation apparatus. As mentioned above, the ventilation connector 206 is capable of receiving within itself at least a portion of an inner tube 24 of a conventional ventilation monitor 16 as illustrated in FIG. 6. An outer tube 26 of the ventilation monitor 16 receives a portion of the ventilation connector 206 to form a press-fit connection. As described above, it is also possible to place a further ring 144 within the ventilation connector 206 in order to minimize deadspace.

The device 200 also includes a suction access tube 208. As with suction access 160 described above, suction access 208 is configured to receive a conventional sleeved suction catheter 30. The suction catheter 30 is press fit onto the suction access 208. The suction access passage 218 is particularly configured such that a suction catheter tube 32 can move freely through the passage 218, through the central housing 202 and out of the passage 216.

The central housing 202 includes means for substantially minimizing or reducing deadspace. As illustrated in FIG. 8 that means comprises configuring internal walls 205 in such a manner that a suction catheter can move freely through the central housing 202, but such that space which would otherwise constitute excess deadspace is filled by the walls 205.

The manner of operation of device 200 can be more fully appreciated with reference to FIG. 9. FIG. 9 is an exploded view of the adaptor device 200 and the associated attachments for use in a typical ventilator circuit. A conventional sleeved suction catheter 30 is shown in position to be attached to the suction access tube 208. As mentioned above, a press fitting is possible, while at the same time minimizing the deadspace within the connection. Within suction access tube 208 there is only sufficient space with the suction catheter 32 to move unobstructed through the device 200.

Also illustrated in FIG. 9 is a monitor 16. As discussed in detail above, the monitor 16 is in turn attached to a ventilator device (not shown). In some instances it may be desirable to connect the ventilator device directly to the ventilator connector 206. This is also possible using the present invention. As with the other connections described herein, the monitor or ventilator may be connected to the device 200 through a convenient press fit.

An endotracheal tube 10 is also illustrated in position for attachment to the endotracheal connector 204. The endotracheal tube 10 is attached to the endotracheal connector 204 in the manner described with reference to FIGS. 3–7. Thus, a secure attachment is achieved while at the same time minimizing deadspace within the overall system.

The final components illustrated in FIG. 9 are a lavage port 220 and a lavage valve 222. The lavage port is used to introduce various fluids into the system. For example, it may be used to introduce saline into a patient's airway. This fluid is generally used to dislodge airway secretions during treatment.

The lavage valve 222 is fitted into the lavage port 220. The lavage valve 222 is normally capped. When it is necessary to lavage the patient, the cap is simply opened and the desired fluid introduced. It is not necessary to interrupt the treatment of the patient in any significant way.

In summary, the neonatal suction adaptor of the present invention has several advantageous features. Because neonatal patients have relatively small tidal volumes, a difference in ventilation circuit deadspace of only a few cubic centimeters can make the difference between effective ventilation of the patient, on the one hand, and injuries caused by lack of oxygen, on the other. The adaptor of the present invention has a smaller deadspace than conventional neonatal suction adaptors, and is therefore useful in situations where conventional adaptors are ineffective.

The present adaptor not only recognizes the crucial importance of deadspace relative to tidal volume, but also employs a variety of features to reduce deadspace. These includes utilizing a narrow core passage; employing a flexible valve to separate the suction access passage from the central chamber; receiving portions of conventional monitors and tubes into the ventilation connector passage and the endotracheal connector annular recess; filling potential deadspace with the core; and utilizing plugs and reducer tubes.

The suction access passage and the core passage of the present adaptor are also aligned, thereby permitting a catheter tube to travel in a substantially straight line in and out of the endotracheal tube. This reduces the risk of kinks in the catheter tube and the endotracheal tube. The adaptor is easily connected by press-fit connections with a wide variety of conventional sleeved neonatal suction catheters, ventilation monitors, and endotracheal tubes to form a closed system. The adaptor is also compatible with conventional exposed catheters.

The adaptor allows tidal volume monitoring and synchronization to continue without substantial interference while a suction catheter is used. Thus, the adaptor reduces the risk of anoxia, heart failure, pressure necrosis, and other adverse effects of conventional suction adaptor usage.

The invention may be embodied in other specific forms without departing from its spirit or essential characteristics. The described embodiments are to be considered in all respects only as illustrative and not restrictive. Any explanations provided herein of the scientific principles employed in the present invention are illustrative only. The scope of the invention is, therefore, indicated by the appended claims rather than by the foregoing description. All changes which come within the meaning and range of equivalency of the claims are to be embraced within their scope.

What is claimed and desired to be secured by patent is:

1. An adaptor for use in a neonatal ventilation circuit, said adaptor comprising:

a central housing disposed about and substantially defining a central chamber and means for substantially reducing the internal volume of said central chamber;

an endotracheal connector secured to and extending from said central housing, said endotracheal connector having a passage which is in fluid communication with said central chamber and means for removably securing an endotracheal tube to said endotracheal connector, while at the same time substantially minimizing the deadspace produced by said connection;

a suction access tube secured to and extending from said central housing, said suction access tube having a suction access passage which is in fluid communication with said central chamber, said suction access tube having means for removably securing a suction tube to said suction access tube while allowing passage of a suction catheter through said suction tube and at the same time minimizing the deadspace produced by said connection; and a ventilation connector secured to and extending from said central housing, said ventilation connector comprising a tube having a ventilation passage which is in fluid communication with said central chamber, said ventilation connection further having means for removably securing a ventilator while at the same time substantially minimizing the deadspace produced by said connection.

2. The adaptor of claim 1, wherein the total volume of said central chamber and said core passage is no greater than about one cubic centimeter.

3. The adaptor of claim 1, wherein the total volume of said central chamber and said core passage is in the range from about 0.4 cubic centimeters to about 0.6 cubic centimeters.

4. The adaptor of claim 1, wherein the effective internal volume of said adaptor is no greater than about one cubic centimeter if said adaptor is connected to an endotracheal tube ventilation adaptor, a suction catheter, and a ventilation monitor.

5. The adaptor of claim 1, wherein the effective internal volume of said adaptor is in the range from about 0.4 cubic centimeters to about 0.6 cubic centimeters if said adaptor is connected to an endotracheal tube ventilation adaptor, a suction catheter, and a ventilation monitor.

6. The adaptor of claim 1, wherein said ventilation passage is substantially transverse to said passage of said endotracheal connector and to said suction access passage.

7. The adaptor of claim 1, wherein said endotracheal connector comprises a sleeve disposed about a core, said sleeve being separated from said core to thereby substantially define an annular recess, said passage of said endotracheal connector comprising a core passage within said core, and said core passage being in fluid communication with said central chamber such that the deadspace within said endotracheal connector is substantially minimized.

8. The adaptor of claim 1, wherein said ventilation passage is substantially perpendicular to said passage of said endotracheal connector and is also substantially perpendicular to said suction access passage.

9. The adaptor of claim 1, wherein said endotracheal connector comprises a press-fit connector that is capable of releasably engaging an endotracheal tube.

10. The adaptor of claim 1, wherein said endotracheal connector comprises a press-fit connector that is capable of releasably engaging an endotracheal tube, the endotracheal tube including a cylindrical extension, and said annular recess of said endotracheal connector being capable of receiving in releasable engagement at least a portion of the cylindrical extension so as to substantially minimize the deadspace produced by said connection.

11. The adaptor of claim 1, wherein said ventilation connector tube comprises a press-fit connector that is capable of releasably engaging a ventilation monitor.

12. The adaptor of claim 11, wherein such a ventilation monitor includes an outer tube which is disposed around an inner tube and which is separated from the inner tube by an annular channel, and said connector tube is capable of fitting substantially within the annular channel so as to substantially minimize the deadspace produced by said connection between said adaptor and said monitor.

13. The adaptor of claim 1, wherein said central housing has a valve recess adjoining said central chamber, and said valve recess is configured to receive and retain a portion of a flexible valve.

14. The adaptor of claim 13, wherein said adaptor further comprises a flexible valve, and said valve being positioned to restrict air flow from said central chamber to said suction access passage.

15. The adaptor of claim 1, wherein the exterior of said central housing has at least two opposing grooves for releasably engaging the arms of a U-shaped adaptor holder.

16. An adaptor for use in a neonatal ventilation circuit, said adaptor comprising:

a central housing disposed about and substantially defining a central chamber, said central chamber having a volume no greater than about one cubic centimeter;

an endotracheal connector secured to and extending from said central housing, said endotracheal connector comprising a sleeve disposed about a core, said sleeve being separated from said core to thereby substantially define an annular recess, said core having a core passage which is in fluid communication with said central chamber;

a suction access tube secured to and extending from said central housing, said suction access tube having a suction access passage which is in fluid communication with said central chamber said suction access tube having means for removably securing a suction tube to said suction access tube while allowing passage of a suction catheter through said suction tube and at the same time substantially reducing the deadspace produced by said connection; and a ventilation connector secured to and extending from said central housing, said ventilation connector comprising a tube having a ventilation passage which is in fluid communication with said central chamber, said ventilation connection further having means for removably securing a ventilator while at the same time substantially reducing the deadspace produced by said connection.

17. The adaptor of claim 16, wherein the total volume of said central chamber and said core passage is in the range from about 0.4 cubic centimeters to about 0.6 cubic centimeters.

18. The adaptor of claim 16, wherein the effective internal volume of said adaptor is in the range from about 0.4 cubic centimeters to about 0.6 cubic centimeters cubic centimeters if said adaptor is connected to an endotracheal tube ventilation adaptor, a suction catheter, and a ventilation monitor.

19. The adaptor of claim 16, wherein the exterior of said central housing has at least two opposing grooves for releasably engaging the arms of a U-shaped adaptor holder.

20. An adaptor for use in a neonatal ventilation circuit, said adaptor comprising:

a central housing disposed about and substantially defining a central chamber, said central chamber having a volume in the range from about 0.4 cubic centimeters to about 0.6 cubic centimeters;

an endotracheal connector secured to and extending from said central housing, said endotracheal connector comprising a sleeve disposed about a core, said sleeve being separated from said core to thereby substantially define an annular recess, said core having a core passage which is in fluid communication with said central chamber;

a suction access tube secured to and extending from said central housing, said suction access tube having a suction access passage which is in fluid communication with said central chamber and which is substantially parallel to said core passage of said endotracheal connector;

a ventilation connector secured to and extending from said central housing, said ventilation connector comprising a tube having a ventilation passage which is in fluid communication with said central chamber;

said adaptor configured such that deadspace within the central chamber is maintained at a predetermined volume in the range of from about 0.4 cubic centimeters to about 1.0 cubic centimeters.

* * * * *